United States Patent [19]

Spaulding

[11] Patent Number: 5,439,362

[45] Date of Patent: Aug. 8, 1995

[54] SEX-ASSOCIATED MEMBRANE PROTEINS AND METHODS FOR INCREASING THE PROBABILITY THAT OFFSPRING WILL BE OF A DESIRED SEX

[75] Inventor: Glenn F. Spaulding, Chandler, Ariz.

[73] Assignee: Cytogam, Inc., Chandler, Ariz.

[21] Appl. No.: 280,637

[22] Filed: Jul. 25, 1994

Related U.S. Application Data

[60] Division of Ser. No. 667,974, Mar. 12, 1991, Pat. No. 5,346,990, which is a division of Ser. No. 351,642, May 12, 1989, Pat. No. 5,021,244, which is a continuation-in-part of Ser. No. 282,922, Dec. 6, 1988, abandoned, which is a continuation of Ser. No. 35,986, Apr. 8, 1987, abandoned.

[51] Int. Cl.$^6$ .................. A61K 35/52; G01N 21/64
[52] U.S. Cl. ................... 424/185.1; 424/811; 424/152.1; 424/172.1; 424/184.1; 514/21; 435/2; 530/350; 530/388.2; 530/389.1
[58] Field of Search .......... 530/350, 388.2, 389.1; 435/2; 424/152.1, 172.1, 811, 185.1, 184.1; 514/21

[56] References Cited

U.S. PATENT DOCUMENTS

| | | | |
|---|---|---|---|
| 3,687,806 | 8/1972 | Van Den Bovenkamp | 435/2 |
| 3,692,897 | 9/1972 | Bhattacharya et al. | 364/579 |
| 3,906,929 | 9/1975 | Augspurger | 600/34 |
| 4,083,957 | 4/1978 | Lang | 435/30 |
| 4,085,205 | 4/1978 | Hancock | 424/172.1 |
| 4,191,749 | 3/1980 | Bryant | 424/811 |
| 4,362,246 | 12/1982 | Adair | 209/3.3 |
| 4,448,767 | 5/1984 | Bryant | 424/811 |
| 4,474,875 | 10/1984 | Shrimpton | 435/2 |
| 4,680,258 | 7/1987 | Hammerling et al. | 435/2 |
| 4,722,887 | 2/1988 | Fabricant et al. | 424/811 |
| 4,769,319 | 9/1988 | Ellis et al. | 435/6 |
| 4,770,992 | 9/1988 | Van den Engh et al. | 435/6 |
| 5,021,244 | 6/1991 | Spaulding | 424/811 |
| 5,346,990 | 9/1994 | Spaulding | 424/811 |

FOREIGN PATENT DOCUMENTS

| | | |
|---|---|---|
| 1148082 | 6/1983 | Canada . |
| 213391 | 3/1987 | European Pat. Off. . |
| 251710 | 1/1988 | European Pat. Off. . |
| WO84/01265 | 4/1984 | WIPO . |
| WO90/13303 | 11/1990 | WIPO . |

OTHER PUBLICATIONS

N. J. Alexander and D. J. Anderson, "Immunology of Semen", *Fert. and Steril.*, 47, pp. 192–205 (1987).

G. F. Ames and K. Nikaido, "Two-Dimensional Gel Electrophoresis Of Membrane Proteins", *Biochem.* 15, pp. 616–623 (1976).

G. B. Anderson, "Identification Of Embryonic Sex By Detection of H-Y Antigen", *Theriog.*, 27, pp. 81–97 (1987).

(List continued on next page.)

*Primary Examiner*—Howard E. Schain
*Assistant Examiner*—P. Lynn Touzeau
*Attorney, Agent, or Firm*—Fish & Neave; James F. Haley, Jr.; Mary Anne Schofield

[57] ABSTRACT

A method of sorting living cells based on DNA content. Mammalian sperm subpopulations enriched in X- or Y-sperm. X- and Y-enriched sperm-plasma-membrane vesicles. Substantially pure sex-associated membrane (SAM) proteins. Antibodies binding to X- or Y-SAM proteins, essentially free of antibodies binding to Y- or X-SAM proteins respectively, or to the H-Y antigen. Semen samples enriched for X- or Y-sperm. Methods for increasing the probability that offspring will be male or female comprising the step of allowing as sperm from an enriched semen sample to fertilize an ovum. Methods for increasing the probability that offspring will be male or female comprising the step of immunizing a female with X- or Y-SAM proteins. Methods of decreasing fertility comprising the step of immunizing a female with both X- and Y-sperm. Methods of increasing the probability that mammalian offspring will carry a gene for a particular sex-chromosome linked trait.

7 Claims, No Drawings

OTHER PUBLICATIONS

*D. Bennett and E. Boyse, "Sex Ratio In Progeny Of Mice Inseminated With Sperm Treated With H-Y Antiserum", *Nature*, 246, pp. 308–309 (1973).

D. Bennett and R. S. Johnson, "Biotech Experts Report Progress In Agricultural Research", in Genetic Engineering News, Sep. (1985).

R. E. Billingham and W. K. Silvers, "Induction of Tolerance Of Skin Isografts From Male Donors In Female Mice", *Science*, 128, pp. 780–781 (1958) (Billingham-I).

R. E. Billingham et al. "A Second Study On The H-Y Transplantation Antigen In Mice", *Proc. Royal Society of London, Series B, Biol. Sci.*, 163 (1990), pp. 61–89 (1965) pertinent.

H. von Boehmer "Fine Specificity Of A Continuously Growing Killer Cell Clone Specific For H-Y Antigen", *Eur. J. Immunol.*, 9, pp. 592–597 (1979).

E. A. Boyse and D. Bennett, "Differentiation And The Cell Surface; Illustrations From Work With T Cells And Sperm", in *Cellular Selection and Regulation In The Immune Response*, G. M. Edelman ed., Raven Press, New York, pp. 155–176 (1974).

F. Bradley et al., "Structural Proteins Of The Mouse Spermatozoan Tail: An Electrophoretic Analysis", *Biol. Reprod.*, 24, pp. 691–701 (1981).

M. P. Bradley and B. F. Heslop, "A Biochemical And Immunological Approach To The Identification Of H-Y Antigenic Proteins Secreted From Daudi Cells", *Hum. Genet.*, 71, pp. 117–121, (1985).

B. F. Brandriff et al., "Sex Chromosome Ratios Determined By Karyotypic Analysis In Albumin-Isolated Human Sperm", *Fertil. Steril.*, 46, pp. 678–685 (1986).

*G. Braun et al., "Method and Apparatus for Fluorometric Determination of the Amount of Material Embedded in Particles", Appl. 260,742, (1984), *Chem. Abstracts*, 104, #17532e, p. 282 (1986) (Braun).

M. Brunner et al., "On The Secretion of H-Y Antigen", *Cell*, 37, pp. 615–619 (1984).

*D. N. Crichton and B. B. Cohen, "Analysis Of The Murine Sperm Surface With Monoclonal Antibodies", *J. Reprod. Fert.*, 68, pp. 497–505 (1983).

*W. P. Dmowski et al., "Use Of Albumin Gradients For X and Y Sperm Separation And Clinical Experience With Male Sex Preselection", *Fertil. Steril.*, 31, pp. 52–57 (1979).

E. M. Eddy and J. K. Koehler, "Restricted Domains Of The Sperm Surface" in *Scanning Electron Microscopy*, Sem. Inc. AMF O'Hare, Ill. pp. 1313–1323 (1982).

*R. J. Ericsson et al., "Isolation Of Fractions Rich In Human Y Sperm", *Nature*, 246, pp. 421–424 (1983).

H. J. Evans, "Properties of Human X and Y Sperm", *Proc. Int. Symp. Gen. Sperm.*, pp. 144–159 (1972).

"Farm Flashes . . . Seasonal Reminders and Research: Machine Sorts Semen For Sex Selection", *Hoard's Dairyman*, Mar. 25, 1988.

E. H. E. Frost et al., "Radioactive Labelling of Viruses: An Iodination Technique Preserving Biological Properties", *J. Gen. Virol.*, 35, pp. 181–185 (1977).

D. L. Garner et al., "Quantification Of The X-and Y-Chromosome-Bearing Spermatozoa of Domestic Animals By Flow Cytometry", *Biol. Repro.*, 28, pp. 312–321 (1983) (Garner-I).

*D. L. Garner et al., "An Overview of Separation of X- and Y-Spermatozoa", *Proceedings of the Tenth Technical Conference on Artificial Insemination and Reproduction* (National Association of Animal Breeders), pp. 87–92 (1984) (Garner-II).

G. Gillis et al., "Isolation And Characterization Of Membrane Vesicles From Human And Boar Spermatozoa: Methods Using Nitrogen Cavitation And Ionophore Induced Vesiculation", *Prep. Bioch.*, 8, pp. 363–378 (1978).

*B. Gledhill, "Cytometry Of Mammalian Sperm", *Gamete Research*, 12, pp. 423–438 (1985) (Gledhill I).

B. L. Gledhill, "Selection and Separation of X- and Y-Chromosome-Bearing Mammalian Sperm", *Gamete Res.*, 20, pp. 377–395 (1988) (Gledhill II).

E. H. Goldberg et al., "Serological Demonstration Of H-Y (Male) Antigen On Mouse Sperm", *Nature*, 232, pp. 478–480 (1971) (Goldberg-I).

E. Goldberg, "Current Status Of Research On Sperm Antigens: Potential Applications As Contraceptive Vaccines", *Res. Front. Fert. Reg.*, 2, pp. 1–11 (1983) (Goldberg-II).

Hafs and Boyd, "Sex Ratio at Birth—Prospects for Control" *Am. Soc. Anim. Sci.* pp. 85–97 (1971).

J. I. Hall and S. S. Wachtel, "Primary Sex Determination: Genetics And Biochemistry", *Mol. Cell. Biochem.*, 33, pp. 49–66 (1980).

(List continued on next page.)

OTHER PUBLICATIONS

T. S. Hauschka and B. A. Holdridge, "A Cytogenetic Approach To The Y-Linked Histocompatibility Antigen Of Mice", *Ann. N.Y. Acad. Sci.*, 101, pp. 12–23 (1962).

U. Hegde et al., "Phytohaemagglutinin As A Molecular Probe To Study The Membrane Constituents Of Human X-And Y-Bearing Spermatozoa", *J. Rep. Immun.*, 2, pp. 351–357 (1981).

A. C. Hinrichsen-Kohane, "Analysis Of Antigen Expression On Human Spermatozoa By Means Of Monoclonal Antibodies", *Fertil. Steril.*, 43, pp. 279–285 (1985).

*P. Hoppe and G. C. Koo, "Reacting Mouse Sperm With Monoclonal H-Y antibodies Does Not Influence Sex Ratio Of Eggs Fertilized In Vitro", *J. Rep. Immun.*, 6, pp. 1–9 (1984).

E. N. Hughes and J. T. August, "Characterization Of Plasma Membrane Proteins Identified By Monoclonal Antibodies", *J. Biol. Chem.*, 256, pp. 664–671 (1981).

**W. P. Hunt et al., "Isolation of Major Proteins from Boar Sperm Plasma Membranes by Preparative Gel Electrophoresis and Localization of a Major Polypeptide Using Specific Monoclonal Antibodies", *Prep. Biochem.*, 15, pp. 9–33 (1985) (Hunt).

***L. A. Johnson et al., "Flow Sorting of X and Y Chormosome-Bearing Spermatozoa Into Two Populations", *Gamete Research*, 16, pp. 1–9 (1987) (copy enclosed).

L. A. Johnson and D. Pinkel, "Modification Of A Laser-Based Flow Cytometer For High Resolution DNA Analysis Of Mammalian Spermatozoa", *Cytom.*, 7, pp. 268–273 (1986).

*D. J. Arndt-Jovin and T. Jovin, "Analysis And Sorting Of Living Cells According To Deoxyribonucleic Acid Content", *J. Histochem. Cytochem.*, 25, 585–589 (1977).

*G. P. R. Kaiser et al., "Relative Increase in Y-Chromatin-Bearing Spermatozoa After In Vitro Penetration into Human Cervical Mucus", *IRCS*, 2, p. 1100 (1974).

*G. C. Koo et al., "Expression Of H-Y Antigen During Spermatogensis", *Immunogen.*, 9, pp. 293–296 (1979) (Koo-I).

G. C. Koo et al., "Topographical Loacation Of H-Y Antigen On Mouse Spermatozoa By Immunoelectronmicroscopy", *Proc. Nat. Acad. Sci.*, 70, pp. 1502–1505 (1973) (Koo-II).

G. C. Koo and A. Varano, "Inhibition Of H-Y Cell-Mediated Cytolysis By Monoclonal H-Y Specific Antibody", *Immunogen.*, 14, pp. 183–188 (1981) (Koo III).

G. C. Koo and C. Goldberg, "A Simplified Technique For H-Y Typing", *J. Immunol. Methods*, 9, pp. 197–201 (1978) (Koo IV).

U. K. Laemmli, "Cleavage of Structural Proteins during the Assembly of the Head of Bacteriophage T4", *Nature*, 227, pp. 680–685 (1970).

R. Gore-Langton et al., "The Absence Of Specific Interactions Of Sertoli-Cell-Secreted Proteins With Antibodies Directed Against H-Y Antigen", *Cell*, 42, pp. 289–301 (1983).

C. Gregory-Lee et al., "Monoclonal Antibodies To Human Sperm Antigens", *J. Repr. Immun.*, 4, pp. 173–181 (1982).

C. A. Lingwood et al., "The Preparation of Rabbit Antiserum Specific for Mammalian Testicular Sulfogalactoglycerolipid", *J. Immunol.*, 124, pp. 769–774 (1980) (Lingwood-I).

C. Lingwood et al., "Tissue Distribution of Sulfolipids in the Rat. Restricted Location of Sulfatoxygalactosylacylalkylglycerol", *Can. J. Biochem.*, 59, pp. 556–563 (1981) (Lingwood-II).

C. Lingwood and H. Schachter, "Localization of Sulfatoxygalactosylacylalkylglycerol at the Surface of Rat Testicular Germinal Cells by Immunocytochemical Techniques: pH Dependence of a Nonimmunological Reaction Between Immunoglobulin and Germinal Cells", *J. Cell Biol.*, 89, pp. 621–630 (1981) (Lingwood-III).

*R. McCormick et al., "Sex Preselection In The Rabbit Via Immunological Or Immunosedimentation Techniques", *Infert.* 5, pp. 217–227 (1982).

D. H. Moore, II and B. L. Gledhill, "How Large Should My Study Be so That I Can Detect an Altered Sex Ratio?", *Fert. and Steril.*, 50, pp. 21–25 (1988).

G. P. M. Moore, "DNA-Dependent RNA Synthesis In Fixed Cells During Spermatogenesis In Mouse", *Exptl. Cell Res.*, 68, pp. 462–465 (1971).

(List continued on next page.)

OTHER PUBLICATIONS

*J. M. Morrell et al., "Sexing of Sperm by Flow Cytometry", *Vet. Record.*, 122, pp. 322–324 (1988).

Y. Nagai et al., "Testis-Organizing H–Y Antigen Of Man May Lose Its Receptor Binding Activity While Retaining Antigenic Determinants", in *Testicular Development, Structure and Function*, ed. A. Steinberger and E. Steinberger, Raven Press, N.Y., pp. 41–46 (1980) (Nagai-I).

Y. Nagai et al., "The Identification Of Human H–Y Antigen And Testicular Transformation Induced By Its Interaction With The Receptor Site Of Bovine Fetal Ovarian Cells", *Differen.*, 13, pp. 155–164 (1979) (Nagai-II).

T. Noland et al., "Purification And Partial Characterization Of Plasma Membranes From Bovine Spermatozoa", *Biol. Reprod.*, 29, pp. 987–998 (1983) (Noland-I).

T. Noland et al., "Protein Phosphorylation Of Plasma Membranes From Bovine Epididymal Spermatozoa", *Biol. Reprod.*, 31, pp. 185–194 (1984) (Noland-II).

D. A. O'Brien and A. R. Bellve, "Protein Constituents Of The Mouse Spermatozoan", *Develop. Biol.* 75, pp. 386–404 (1980).

S. Ohno et al., "Testis-Organizing H–Y Antigen As A Discrete Protein; Its MHC Restricted Immune Recognition And The Genomic Environment In Which H–Y Gene Operates", *Hum. Genet.*, 58, pp. 37–45 (1981).

Pearson et al., "Chromosomal Studies on Human Male Gametes", *Pro. Symp. Chrom. Errors Rel. Repr. Failure*, Bove and Thibault, ed. Paris, Center Int'l. de L'Enfance pp. 219–227 (1973).

R. Peterson et al., "the Effects Of Antisperm Plasma Membrane Antibodies On Sperm-Egg Binding, Penetration, And Fertilization In the Pig", *J. Exp. Zool*, 223, pp. 79–81 (1982) (Peterson-I).

R. Peterson et al., "Electrophoretic And Chromatographic Properties Of Boar Sperm Plasma Membranes: Antigens And Polypeptides With Affinity for Isolated Zonae Pellucidae", *J. Androl.*, 2, pp. 300–311 (1981) (Peterson-II).

R. Peterson et al., "The Interaction Of Living Boar Sperm And Sperm Plasma Membrane Vesicles With The Porcine Zona Pellucida", *Develop. Biol.*, 84, pp. 144–156 (1981) (Peterson-II).

R. Peterson et al., "Evaluation Of The Purity Of Boar Sperm Plasma Membranes Prepared By Nitrogen Cavitation", *Biol. Reprod.*, 23, pp. 637–645 (1980) (Peterson-IV).

**R. N. Peterson et al., "Characterization of Boar Sperm Plasma Membranes by Two-Dimensional Page and Isolation of Specific Groups of Polypeptides by Anion-Exchange Chromatography and Lectin Affinity Chromatography", *J. Androl.*, 4, pp. 71–81 (1983) (Peterson V).

**R. N. Peterson et al., "Further Characterization of Boar Sperm Plasma Membrane Proteins with Affinity for the Porcine Zona Pellucida", *Gamete Res.*, 12, pp. 91–100 (1985) (Petrson VI).

D. Pinkel et al., "Sex Preselection In Mammals? Separation Of Sperm Bearing Y and O Chromosomes In The Vole Microtus Oregoni", *Science*, 218, pp. 904–906 (1982) (Pinkel-I)

*D. Pinkel et al. "Flow Cytometric Determination Of The Proportions of X– and Y-Chromosome Bearing Sperm In Samples Of Purportedly Separated Bull Sperm", *J. Animal Scien.*, 60, pp. 1303–1307 (1985) (Pinkel-II).

L. D. Russell et al., "Electrophoretic Map Of Boar Sperm Plasma Membrane Polypeptides And Localization And Fractionation Of Specific Polypeptide Subclasses", *Biol. Reprod.*, 28, pp. 393–413 (1983).

**F. Saji et al., "A Human Sperm Coating Antigen Isolated from Sperm Cell Membrane", *Am. J. Reprod. Immunol. Microbiol.*, 8, pp. 132–136 (1985) (Sagi).

W. Schaffner and C. Weissmann, "A Rapid, Sensitive, and Specific Method for the Detrmination of Protein in Dilute Solution", *Anal. Biochem.*, 56, pp. 502–514 (1973).

M. Scheid et al., "Serologically Demonstrable Alloantigens of Mouse Epidermal Cells", i J. Exp. Med., 135, pp. 938–955 (1972).

*E. Schilling, "Sedimentation As An Approach To The Problem Of Separating X–And Y-Chromosome-Bearing Spermatozoa", *Symposium Am. Soc. Anim. Science*, pp. 76–84 (1971).

E. Schmell et al., "Identification Of Mammalian Sperm Surface Antigens. I.Production Of Monoclonal Anti- (List continued on next page.)

OTHER PUBLICATIONS

-mouse Sperm Antibodies", *Fertil. Seril.*, 37, pp. 249-257 (1982) (Schmell-I).

E. Schmell et al., "Identification Of Mammalian Sperm Surface Antigens, II.Characterization Of An Acrosomal Cap Protein And A Tail Protein Using Monoclonal Anti-mouse Sperm Antibodies", *J. Reprod. Immunol.*, 4, pp. 91-106 (1982) (Schmell-II).

M. Shapiro and R. P. Erickson, "Evidence That The Serological Determinant Of H-Y Antigen Is Carbohydrate", *Nature*, 290, pp. 503-505 (1981).

M. A. Shirley and H. Schachter, "Enrichment of Sulfogalctosylalkylacylgylcerol in a Plasma Membrane Fraction from Adult Rat Testis", *Can. J. Biochem.*, 58, pp. 1230-1239 (1980).

E. Simpson, "The H-Y Antigen And Sex Reversal", *Cell*, 44, pp. 813-814 (1986) (Simpson-I).

E. Simpson et al., "Separation Of The Genetic Loci For The H-Y Antigen And For Testis Determination On Human Y Chromosome", *Nature*, 326, pp. 876-877 (1987) (Simpson-II).

R. Stambaugh and J. Buckley, "Association Of The Lactic Dehydrogenase X4 Isozyme With Male-Producing Rabbit Spermatozoa", *J. Reprod. Fert.*, 25, pp. 275-278 (1971).

P. Stanley and E. A. Haslam, "The Polypeptides of Influenza Virus: V. Localization of Polypeptides in the Virion by Iodination Techniques", *Virology*, 46, pp. 761-763 (1971).

R. Stovel et al., "A Means For Orienting Flat Cells In Flow Systems", *J. Biophys.*, 23, pp. 1-5 (1978).

*A. T. Sumner et al., "Distinguishing Between X, Y and YY-bearing Human Spermatozoa By Fluorescence and DNA Content" *Nature* (New Biol.), 229, pp. 231-233 (1971).

H. Towbin et al., "Electrophoretic Transfer of Proteins from Polyacrylamide Gels to Nitrocellulose Sheets: Procedure and Some Applications", *Proc. Natl. Acad. Sci. U.S.A.*, 76, pp. 4350-4354 (1979).

S. Wachtel, "H-Y Antigen And The Genetics Of Sex Determination", *Science*, 198, pp. 797-799 (1977) ("Wachtel-I").

S. Wachtel, "Possible Role For H-Y Antigen In The Primary Determination Of Sex", *Nature*, 257, pp. 235-236 (1975) (Wachtel-II).

*S. Wachtel, "H-Y Antigen In The Study Of Sex Determination And Control Of Sex Ratio", *Theriog.*, 21, pp. 18-28 (1984) (Wachtel-III).

S. Wachtel et al., "Continued Expression Of H-Y Antigen On Male Lymphoid Cells Resident In Female Mice", *Nature*, 244, pp. 102-103 (1973) (Wachtel-IV).

S. Wachtel et al., "Serological Crossreactivity Between H-Y (Male) Antigens Of Mouse and Man", *Proc. Natl. Acad. Sci. USA*, 71, pp. 1215-1218 (1974) (Wachtel-V).

W. Wray et al., "Silver Staining Proteins in Polyacrylamide Gels", *Anal. Biochem.*, 118, pp. 197-203 (1981).

**Y. C. Yan et al., "Monoclonal Antibody Inducing Sperm Agglutination", *Am. J. Reprod. Immunol.*, 4, pp. 111-115 (1983) (*Yan*).

*P. Zavos, "Preconception Sex Determination Via Intra-Vaginal Administration Of H-Y Antisera In Rabbits", *Theriog.*, 20, pp. 235-241 (1983).

L. A. Johnson, "Separation of X and Y Chromosome Bearing Sperm by DNA Content Using Flow Cytometric Analysis and Sorting," *Society for the Study of Reproduction, 20th Anniversary Meeting*, Jul. 20-23, 1987, Urbana, Ill., USA, vol. 36, Supp. No. 1, p. 80, Abstr. 100 (1987).

J. R. Schnieders and P. K. Bajpai, "Effect Of Antisperm Antibodies On Oxygen Utilization And Lactic Acid Production By Human Spermatozoa", IRCS Libr. Compend., 2, p. 1615 (1974) in *Chem. Abst.*, 82, p. 15069 (1975).

*P. Suopart, "MGA-M Appearance in Ejaculated Human Sperm", *Eighth Ann. Meeting Society Study Reprod.*, Fort Collins, Colo. Abstr. 133 (1975).

SEX-ASSOCIATED MEMBRANE PROTEINS AND METHODS FOR INCREASING THE PROBABILITY THAT OFFSPRING WILL BE OF A DESIRED SEX

CROSS REFERENCE TO RELATED APPLICATION

This application is a division of application Ser. No. 07/667,974, filed Mar. 12, 1991, now U.S. Pat. No. 5,346,970, which is a division of application Ser. No. 07/351,642, filed May 12, 1989, now U.S. Pat. No. 5,021,244, which is a continuation-in-part of application Ser. No. 07/282,922, filed Dec. 6, 1988, now abandoned, which is a continuation of application Ser. No. 07/035,986, filed Apr. 4, 1987, now abandoned.

FIELD OF INVENTION

The field of this invention is the isolation of novel proteins and their use in methods to increase the probability that mammalian offspring produced by it will be of a desired sex or carry a gone for a particular sex-chromosome linked trait. This invention relates to sorting of sperm cells into X-enriched and Y-enriched subpopulations. It further relates to the isolation of X-enriched and Y-enriched sperm plasma membranes and components thereof. More particularly, this invention relates to sex-associated membrane proteins and to antibodies which bind to them. It relates to the use of these antibodies to modify a semen sample so that the semen sample will be enriched in X-chromosome bearing sperm cells or Y-chromosome bearing sperm cells.

BACKGROUND OF INVENTION

Mammalian semen contains approximately equal numbers of Y-chromosome bearing sperm cells (Y-sperm) and X-chromosome bearing sperm cells (X-sperm). Fertilization of an ovum by a Y-sperm produces a male. Fertilization by an X-sperm produces a female.

Various methods have been proposed for modifying mammalian semen to increase the relative percentage of X- or Y-sperm in a semen sample, and thereby achieve a greater likelihood of female or male offspring. Attempts to influence or control mammalian sex have not been verifiable. (For reviews of prior research, see Garner, 1984; Pinkel et al., 1985.)

One of the more common approaches for attempting X-sperm or Y-sperm enrichment in semen has relied on motility and density sedimentation. (See Kaiser et al., 1974, or Soupart, 1975.) This approach is based on the Y-sperm's purported greater motility and lighter weight than X-sperm. According to the theory, Y-sperm would penetrate an interface created at two different media densities more easily than X-sperm. One such approach used albumin gradient sedimentation. However, due to the morphological variability of the maturing sperm, no one has independently shown that this technique can separate or enrich X-sperm or Y-sperm (Brandriff et al., 1986).

Immunological methods have also been tried as a means of separating X- and Y-sperm. These methods are based on the fact that spermatid RNA polymerase is capable of transcribing the haploid genome (Moore, 1971). It was believed that X- and Y-sperm could be separated immunologically on the basis of the different antigens produced from this RNA transcript. Antigens investigated in unsexed sperm included the LDH isozyme (Stambaugh and Buckley, 1971). Again, no demonstrable separation has been reported.

Investigators have also looked to the male H-Y antigen as a potential means to enrich sperm subpopulations and thereby preselect sex of offspring. Indirect evidence suggested that H-Y antigen was a cell-surface antigen produced in males but not in females. Accordingly, investigators have reasoned that H-Y is expressed by cells containing a Y chromosome and, therefore, on the surface of Y-sperm but not X-sperm. Consequently, some investigators believed that H-Y antibodies should inactivate Y-sperm but not X-sperm. Some investigators have claimed to skew mammalian sex ratios using methods based on this theory (McCormick et al., 1983; Boyce and Bennet, 1984). Bryant, in particular, has claimed a dramatic skewing of sex ratio using H-Y antibodies (Bryant, U.S. Pat. No. 4,191,749; Bryant, U.S. Pat. No. 4,448,767). However, experience has not borne-out these claims. Hoppe and Koo stated specifically that they were unable to skew sex ratio using antibodies against the H-Y antigen (Hoppe and Koo, 1984). As far as we know, no one has confirmed Bryant's claims.

There may be two reasons for the failure to confirm these results. First, the underlying theory appears to be wrong. The most recent evidence indicates that there is no difference in H-Y presence on mature X- or Y-sperm. While certain male tissues produce H-Y and express it as an integral membrane protein, Y-sperm do not appear to produce H-Y themselves. Rather, both X-and Y-sperm adsorb it to their surface (Garner, 1984). Hoppe and Koo have shown that both X- and Y-sperm react with H-Y antibody (Hoppe and Koo 1984). Our own evidence, which we present herein, corroborates this. Furthermore, Hoppe and Koo showed that as sperm mature, their ability to react with H-Y antigen declines, implying that H-Y is masked or lost from the sperm cell surface (Id.). Second, the experimental technique of some of these investigators may have been flawed. They based their conclusions on experiments with a limited number of animals, so that the sex ratios, while skewed, were not statistically significant (Moore and Gledhill, 1988). Therefore, there is no longer any reason to believe that one could successfully use the H-Y antigen to separate X-sperm and Y-sperm. Indeed, we are not aware of any methods currently in use which successfully use this strategy.

Fabricant et al., U.S. Pat. No. 4,722,887, refers to a method for separating X-and Y-sperm by polymeric phase separation based on differential expression of a sperm cell-surface sulfoglycolipid (SGG). However, the authors state that the evidence for sex-linked differences in this lipid is indirect—it is based on the sex-linked expression of enzymes which metabolize lipid substrates—and the authors express only the expectation that SGG, itself, will prove to be sex-linked.

Another potential separation approach for X-sperm and Y-sperm is based on the known differences in the DNA contents of X-sperm and Y-sperm. Because the DNA content of X-sperm cells is greater than the DNA content of Y-sperm cells, investigators hoped that the respective live cell populations could be separated by density gradient sedimentation or flow cytometry. However, neither has proven to be possible.

One reason for this failure may be that the DNA content differences between X-sperm and Y-sperm are small. For example, the difference is believed to be only about 3.9% for bulls, 3.7% for boars and 4.1% for rams (Sumner 1971; Pearson, et al., 1973; Evans et al., 1972; and Gledhill, 1985). This translates into an approximate 0.003 difference in bouyancy—not enough to permit separation of whole sperm using available methods. While other mammals display somewhat higher differences in the relative DNA contents of X-sperm and Y-sperm, e.g., the vole (*Microtus oregani*) which has about a 9% difference, separation of whole sperm has also not been possible for these animals (see Pinkel et al., 1982). For example, investigators have tried to separate sperm based on their differing DNA content by density gradient sedimentation, but enrichment results could not be verified—one report claims to have slightly enriched a fraction of bull sperm, but not rabbit sperm (Schilling, 1971; Brandriff et al., 1986). Attempted separation on the basis of surface charge density imparted by DNA differences has also been inconsistent (Hafs and Boyd, 1971), or was based upon controversial quinacrine staining (Garner, 1984).

Another reason for these failures may be that the head, tail, and plasma membranes of the sperm, its other cellular material, and its highly compact nucleus all act to mask the small DNA content differences between X-sperm and Y-sperm. Some evidence for this masking effect is the fact that cytometric separation, while not feasible for whole sperm, has been useful to prepare enriched subpopulations of denuded sperm nuclei. Using this technique, the sperm nuclei are first separated from the membranes and other material of whole sperm. They are then stained and partially sorted using a flow cytometer (Johnson and Pinkel, 1986). The result has been nuclei subpopulations enriched for the X- and Y-chromosome.

Investigators have also used this cytometric technique to test the results of various attempts to separate the X- and Y-sperm of whole sperm (a non-enriched sperm population). The Lawrence Livermore National Laboratory and Oklahoma State University made a comparative study of several of the above-described "enrichment" approaches (Pinkel et al., 1985). They analyzed sperm separated by convection-counter-streaming-galvanizaton, albumin gradient, density gradient, electromotility, and anti-H-Y antibodies. The results: "In no case was enrichment of either sperm population observed." (Id. at p. 130.) This finding is consistent with other studies of attempted enrichment: albumin density gradient (Brandriff et al., 1986) and monoclonal anti-H-Y antibodies (Hoppe and Koo, 1984).

Monoclonal antibodies to sperm surface antigens which have heretofore been prepared also do not distinguish X- and Y-sperm. They bind to both X-sperm and Y-sperm, and either inactivate or immobilize both types of sperm cells (Schmell et al., 1982, and Peterson et al., 1981). Monoclonal antibodies appear to inhibit sperm-egg binding without regard to whether they bind to the sperm acrosome, head, midpiece, or tail. Further, antibodies specifically binding to the midpiece or tail have also been observed to immobilize sperm cells. (For a review of antibodies inhibiting fertility see Alexander and Anderson, 1987.)

Prior to this invention, it was not known whether one could isolate subpopulations of cells enriched in either X-sperm or Y-sperm. Nor was it known whether the plasma membranes of these enriched subpopulations would contain unique, sex selective constituents, such as proteins, glycoproteins, or lipoproteins.

In light of these failures, we decided to focus on the sperm cell surface as a possible tool for sperm separation. Studies of the cell membrane of unsexed mammalian sperm indicated that more than 1000 proteins are present on it. See, e.g., Noland et al. (1983 and 1984); (Russell et al., 1983); (Bradley et al., 1981); and (Hughes and August, 1981, and Crichton and Cohen, 1983). All of these studies used mixed membranes of both X- and Y-sperm. Therefore, they failed to distinguish between membranes and constituents characteristic of X-sperm-enriched subpopulations and those of Y-sperm-enriched subpopulations. Consequently, no one, until now, has been able to perform an analysis of X-sperm or Y-sperm membranes, to obtain usable quantities of whole cells enriched for X- or Y-sperm, to identify a sex-chromosome associated membrane protein of mammalian sperm, or to isolate such proteins.

SUMMARY OF INVENTION

It is an object of this invention to provide methods to increase the probability that mammalian offspring will be of a desired sex or carry a gene for a particular sex-chromosome linked trait. This invention achieves this object by providing sex associated membrane (SAM) proteins which are useful as vaccines and to produce antibodies, themselves useful as contraceptives or for providing semen samples enriched in X- or Y-sperm.

The present invention also provides for a method to separate living cells based on DNA content. The method involves separating the cells by flow cytometry, the cytometer having been improved to substantially increase its ability to recognize fine distinctions in fluorescence. Sperm cell populations separated in this manner result in subpopulations enriched in X- and Y-sperm. By isolating the membranes from these enriched subpopulations, one obtains another aspect of this invention: X- and Y-enriched sperm-plasma-membrane vesicles.

This invention also provides for refined and substantially pure sex-associated membrane (SAM) proteins. These proteins are characterized in that when one separates membrane proteins from enriched sperm-plasma-membrane vesicles, SAM proteins are more intense in one profile than the other. Therefore, SAM proteins distinguish X- and Y-sperm from each other.

One may use SAM proteins of this invention to immunize females against X-sperm, Y-sperm, or both, thereby increasing the probability of offspring of a certain sex, or decreasing fertility altogether.

SAM proteins are also useful in preparing another aspect of this invention: monoclonal and polyclonal antibodies that selectively bind to X-and Y-SAM proteins and, therefore, to X- or Y-sperm. One may use these antibodies to produce semen samples enriched for Y- or X-sperm. Upon incubation with antibodies against X- or Y-SAM proteins, the antibodies bind to and inactivate X- or Y-sperm respectively, and prevent them from fertilizing an ovum (Alexander and Anderson, 1987). The sperm cells which have not been bound by the antibodies are left viable and active for fertilizing ova. Therefore, this invention provides for the first time a method to produce a semen sample enriched in active X- or Y-sperm capable of increasing the probability that offspring will be of a desired sex or carry a gene for a sex-chromosome linked trait.

One may also use SAM proteins to detect the presence of anti-SAM antibodies a sample.

The antibodies of this invention are especially useful in methods of artificial insemination. Carrying out this embodiment of the invention, a viable semen sample usable for artificial insemination is mixed either in vitro or in vivo with a sex-selective antibody preparation of this invention. The resulting sample is enriched for X- or Y-sperm. One then uses the sample in the normal way in artificial insemination.

One may use the antibodies of this invention to separate semen into novel X- and Y-containing subpopulations, e.g., by affinity chromotography. These purified subpopulations are then useful in fertilizing ova to produce offspring of the desired sex.

One may also use the antibodies which bind to the SAM proteins of this invention as a contraceptive by contacting sperm with both anti-X- and anti-Y-sperm antibodies.

DETAILED DESCRIPTION OF THIS INVENTION

In order that one may understand the invention described herein more fully, we set forth the following detailed description.

In this specification we mean the term "protein" to include glyco-, lipo-, and phosphoproteins, polypeptides, and peptides, as well as complexes of these molecules.

By the term "refined" we mean proteins as least as pure as obtained by the 1-D gels we describe herein.

By the term "substantially pure" we mean proteins at least as pure as obtained by the 2-D gels we describe herein.

This invention provides for refined or substantially pure sex-associated membrane ("SAM") proteins. SAM proteins are characterized by differential existence on the membranes of X-sperm and Y-sperm, respectively. The SAM proteins of this invention are characterized by a molecular weight (MW) determined by SDS-polyacrylamide gel electrophoresis (PAGE) and isoelectric point (pI) determined on immobilized pH gradient gels (IPG). The SAM proteins of this invention are initially identified by a process comprising the steps of:

(a) sorting mammalian sperm into subpopulations enriched for X-sperm and Y-sperm;

(b) separating the plasma membranes from those enriched subpopulations; and (c) identifying the X- and Y-sex-associated membrane proteins among the plasma membrane proteins of those enriched subpopulations by comparing the relative amounts of protein present in corresponding spots on two dimensional IPG-SDS/PAGE the plasma membrane proteins from whole sperm, the plasma membrane proteins from the X-enriched sperm subpopulation, and the plasma membrane proteins from the Y-enriched sperm subpopulation.

More preferably, the SAM proteins of this invention are initially identified by comparing the relative amounts of protein in corresponding spots on two dimensional IPG-SDS/PAGE profiles of the plasma membrane proteins representing the X-enriched sperm subpopulation and Y-enriched sperm subpopulation. Such two dimensional gels are preferred because they result in the isolation of substantially pure SAM proteins. They separate proteins on the basis of two characteristics—molecular weight and pI. One dimensional gels separate proteins on the basis of a single characteristic—molecular weight or pI. However, one-dimensional gels, such as SDS/PAGE profiles (which separate proteins by molecular weight only) or IPG profiles (which separate proteins based on pI), are also useful in initially identifying the SAM proteins of this invention. The protein bands so identified on 1-D gels contain refined SAM protein but may contain a few other proteins of the same molecular weight. The protein of that band may be used directly as an immunogen. It may also be further purified using conventional protein purification techniques.

In this less preferred embodiment of SDS/PAGE selection, the X-SAM proteins of this invention, thus, are characterized in that they exhibit a higher band density in the plasma membrane proteins prepared from X-enriched sperm subpopulations as compared to the corresponding bands for the plasma membrane proteins from whole sperm and the plasma membrane proteins prepared from Y-enriched sperm subpopulations. Similarly, prepared in this aspect of the invention the Y-SAM proteins of this invention are characterized in that they exhibit a higher band density in the plasma membrane proteins prepared from Y-enriched sperm subpopulations as compared to the corresponding bands for plasma membrane proteins from whole sperm and the plasma membrane proteins prepared from X-enriched sperm subpopulations. More preferably, the X-SAM and Y-SAM proteins of this invention exhibit the above described higher relative spot densities on two dimensional IPG-SDS/PAGE profiles.

After the SAM proteins of this invention are initially identified as described above, one may isolate them in large quantities from the plasma membrane proteins of whole sperm using the molecular weight, pI, or other physical, chemical, or biological characteristics of the initially identified SAM proteins. Thus, an important aspect of this invention is that the time-consuming process of sorting sperm into enriched X- and Y-subpopulations need only be done for initial identification of the SAM proteins of this invention.

One may use the SAM proteins isolated from an nonenriched sperm population or from the enriched sperm subpopulations, as described above, in a variety of ways in accordance with this invention. For example, one may use them to innoculate females, immunizing them against X- or Y-sperm, or both. Also, one may use them to raise antibodies, either polyclonal or monoclonal, using well known conventional techniques. Furthermore, one could use SAM proteins to detect the presence of anti-SAM antibodies in a sample. This could be useful in the diagnosis of infertility.

The novel antibodies produced in these methods selectively bind to proteins on the plasma membranes of either X- or Y-sperm. As such they are useful in modifying semen to preselect the sex of the offspring produced by it. For example, one may use the novel antibodies of this invention in vivo or in vitro to bind either X-sperm or Y-sperm and thus to select the sex of mammalian offspring. The antibodies are especially useful in artificial insemination and in vitro fertilization. They are also useful in purifying X- or Y-SAM proteins or the X- or Y-sperm of whole sperm by, for example, affinity chromatography.

This invention is applicable to a wide variety of species. For example, it is applicable to the commercially important mammalian species—cattle, dogs, cats, horses, swine, and sheep. It is also applicable to humans.

In each of these species there is a DNA content difference of greater than 1% as between X-sperm and Y-sperm. Thus, one may treat sperm from each of these species as described in this invention. In each case the cells may be sorted into X- and Y-sperm enriched subpopulations, the plasma membranes of those enriched subpopulations identified and isolated, and, most preferably, the respective SAM proteins from the plasma membranes of those subpopulations identified and isolated. One may then employ these proteins to produce sex specific antibodies for use in the sex-selective and sex predictive methods and compositions of this invention.

The SAM proteins of this invention are also useful to isolate DNA sequences which code on expression for SAM proteins. For example, one determines a partial amino acid sequence for a SAM protein. Then one synthesizes, as a probe, a DNA sequence encoding that amino acid sequence. One then constructs cDNA library of mRNA from a cell producing SAM proteins. Then one probes the cDNA library with the DNA probe using methods well known to the art. After isolating clones containing cDNA hybridizing to the probe, one identifies those cDNA sequences encoding SAM proteins. One would do this, for example, by expressing the cDNA in a eukaryotic expression system and identifying clones producing protein which binds to anti-SAM protein antibodies.

In the particular embodiment of this invention, specifically exemplified herein, we used bull semen. Bull semen has a DNA content difference between X-sperm and Y-sperm of about 4%. We sorted the sperm of this semen into subpopulations enriched by greater than 68% in either X-sperm or Y-sperm. We then prepared the plasma membranes of these enriched subpopulations and identified the sex-specific components therein. We describe these results in Example II.

We have also used the methods of this invention, as described more fully herein, to identify the plasma membrane proteins of subpopulations of sperm enriched in X-sperm or Y-sperm and the components thereof in another species, the chinchilla. In that species the X-SAM proteins have molecular weights on SDS-PAGE as follows: 33 kD; 39 kD, and 53 kD. The Y-SAM proteins have molecular weights on SDS-PAGE: 17 kD; 31 kD; 36 kD; 41 kD; 42 kD, and 57 kD.

To enable more easily the practice of the present invention, the following detailed directions and experimental results are set out.

EXAMPLE I

Sorting Sperm by Flow Cytometry

To sort mammalian sperm by means of a flow cytometer so as to obtain separate viable cell fractions or subpopulations enriched for X- and Y-sperm, we used equipment and methodology which have not heretofore been known. We now describe an example of one such method.

Flow Cytometer Modifications and Adjustments

To carry out the sperm sorting, we modified a commercially available flow cytometer. Our particular modifications were made on the Epics Model 752 Flow Cytometer sold by the Epics Division of Coulter Electronics, Hialeah, Fla. However, one can make similar modifications to other flow cytometers. Flow cytometers, in general, operate as follows.

The flow cytometer utilizes a laser to interrogate a sample stream of suspended cells contained within an outer sheath fluid. For DNA analysis, these cells are bound with a dye which, in response to ultraviolet laser excitation, emits fluorescent light in proportion to the amount of DNA. A photomultiplier tube arranged orthogonally to both the laser beam and sample stream receives this light. Depending on the amount of DNA detected, one can then separate cells into one of three containers (X, Y, or waste) employing the flow cytometer sorting capability. In this operation, an ultrasonic vibrator breaks the sample stream into individual droplets, each containing an individual cell. The droplets are given a charge based on the DNA content of the cell and are deflected into the appropriate container by an electric field. This instrument is capable of analyzing and sorting cells at rates up to 10,000 cells/second.

We isolated the Model 752 Flow Cytometer from vibrations of greater than 7 Hz by placing the instrument on a fixed rigid tubular frame table equipped with double deflection shear/compression mounts. We further improved flow cytometer resolution by continuously degassing the sheath fluid during the sort. We accomplished this by passing the pressurized sheath fluid through expanded teflon tubing designed for HPLC degassing. We injected cells suspended in Hoechst 33342 DNA stain into the sheath fluid using minimal pressure to reduce the core size of the sample stream. We used a sample insertion tube whose tip was bilaterally beveled and polished to a 20° angle. The tube creates a ribbon shaped sample stream whose flat surface is normal to the long axis of the laser beam (See Stovel et al., 1978). In this geometry, the viable sperm will orient themselves such that their flat faces remain normal to the laser illumination, thereby improving the resolution.

We also made various modifications and adjustments to the electronics of the Model 752 Flow Cytometer: Potentials across the PMT (photomultiplier tube) were set through a resistive voltage divider network of low noise metal film resistors. The signal was current-to-voltage converted utilizing an op amp with characteristics of ultra high speed, wide power band-width, low noise and high linearity, with coaxial capabilities. We used a Fast Fourier Transform (1024 channel) of the signal for the purpose of designing low-pass (1 MHz) and high-pass (100 KHz) filters that bracketed the frequency of the pulses associated with the X- or Y-sperm. Signals representing the DNA were then actively filtered and amplified before 10-bit analog-to-digital conversion (ADC). All filter and amplifier resistors were low-noise metal films tested for linearity across the frequency of use. We set amplifier gains at values of 10 or 20 and set PMT voltages to detect signals in the upper channels of the ADC.

We also made various optical modifications and adjustments to the flow cytometer. We adjusted the laser for the fundamental transverse mode ($TEM_{oo}$) utilizing test microspheres (Epics Grade I Fulbright Beads, CV<1) or a divergent beam. Once adjusted, the laser was peaked and aligned in $TEM_{oo}$ at the power output to be used for sorting (300–400 mW). We initialized optical alignment by first using a thread to confirm that alignment targets were in horizontal alignment with the pinhole leading to the PMT. Confocal optics (Epics) and other light path components were set with the laser serving as a reference point. The fluorescence emission of microspheres resulting from 351 nm laser excitation was detected through a completely light sealed path containing two 408 nm long pass filters, having a signal-to-noise ratio of greater than 1000. We tuned the coefficient of variation (CV) with microspheres to less than 1%. As a result of these modifications, we have been able to improve the signal-to-noise ratio to 1000:1.

In the preferred embodiment of this invention we also replaced the laser following indications of low performance; used a 4 hour warm-up before calibration and sorting; operated the flow cytometer in a 20° C. temperature-stabilized room with black walls and dim lights; and shielded air-flow arising from the machine fan which flowed across the flow chamber.

We were able to resolve X- and Y-sperm peaks, and thereby to sort the two populations, with the following improvements in place: (1) a signal to noise ratio of at least 100:1; (2) a laser power to each cell of at least 90 mW; (3) a PMT quantum efficiency of at least 8%; and (4) cells adjusted to the same orientation. However, we obtained best results when the signal to noise ratio is at least 1000:1; the laser power to each cell is at least 160 mW; and the PMT quantum efficiency is at least 20%.

Preparation of Sperm

Immediately after collection we diluted freshly ejaculated mammalian semen with isoosmotic PBS to 15 ml, and slowly cooled it to 5° C. At this temperature, we washed the sperm three times in isoosmotic, pH 7.2, tris-methylaminomethane buffered saline (TBS) saturated with phenylmethylsulfonylfluoride (PMSF) and 10 µg/ml Hoechst No. 33342 bis benzimide dye. This solution stained cells and simultaneously inhibited enzymatic breakdown. We centrifuged the cells at $483 \times g$ for 20 minutes and resuspended them to remove seminal plasma proteins. We then diluted the washed cells in dye solution to a cell concentration of $20 \times 10^6$ cells/ml and allowed them to stain for a minimum of 2 hours. (See Arndt-Jovin et al., 1977.) The Hoechst dye is available from Calbiochem-Behring Corp., San Diego, Calif. We prepared sheath fluid in the same manner as the solution used to wash sperm, except that the dye was omitted. We degassed the fluid as described above. The objective was to match the refractive indices between sheath and sample fluid.

Sorting of Sperm

We employed the Model 752 Flow Cytometer, modified and adjusted as described above, for sorting sperm. We sorted the sperm based on total DNA content as measured with the aid of the Hoechst dye. X-sperm have more total DNA content than Y-sperm. The mean peak fluorescence arising from X-and Y-sperm from bull, boar, ram, and other large mammals is typically separated by values greater than 3%. The whole sperm as prepared in the solution of TBS/PMSF/stain was analyzed at rates up to 10,000 cells per second. The cytometer sorted these cells into X-enriched, Y-enriched, or waste populations. The X-enriched and Y-enriched populations collected at a rate between 100 and 500 cells/sec. Coincident cells were rejected. The actual flow rate used in any sort depends on the state of the machine, with a reduction in flow rate required to improve resolution. We adjusted the flow rate to observe a plateau on the DNA histogram, indicating the onset of splitting into X and Y peaks. We often set the optimal sheath-to-sample flow at a differential pressure greater than pinch-off by 2 mm Hg. We set sorting gates such that only the cells contained in the outer third of the DNA histogram for oriented X-chromosome bearing and Y-chromosome bearing sperm were collected. The anti-coincidence circuit was preferably active during sorting.

In this way we simultaneously collected two viable subpopulations enriched for X- or Y-sperm, respectively. Each subpopulation had an enrichment of at least 68%. We were also able to obtain Y-sperm subpopulations enriched to 72%. Such concentrations were sufficient for the purpose of the present invention and were used, as will subsequently be described, for isolation and identification of the novel, enriched plasma membranes vesicles and the SAM proteins of this invention. Each milliliter of sorted cells contained approximately 300,000 cells and required about 30 minutes to sort. Roughly $20 \times 10^6$ cells could be collected per week.

EXAMPLE II

Isolation of Sex-Specific Sperm Plasma Membrane Vesicles

We used the X-sperm or Y-sperm enriched cell subpopulations of Example I to isolate plasma membrane vesicles (PMV), and X- and Y-enriched non-membrane sperm component.

We cavitated cell samples containing enriched X-sperm or Y-sperm subpopulations in Parr bombs. Suitable sample sizes were 3 to 10 ml with 50,000 to 500,000 cells/ml. We also cavitated non-enriched sperm samples (50:50 mixture of X- and Y-sperm). We used a cavitation method (at about 650 psi) as described by Gillis, et al., 1978. We separated plasma membrane vesicles consisting of mostly (e.g., 80% (boar sperm data)) head plasma membrane and some (e.g., 20% (boar sperm data)) tail plasma membrane from sperm heads, tails, and other particulates by pelleting centrifugation twice at $2500 \times g$ for 30 minutes. We withdrew the supernatant containing the PMV material and centrifuged it at $100,000 \times g$ to obtain the PMV-material, which we resuspended and washed in 10 mM tris acetate 5.5). This removed most of the TBS/PMSF/stain from the isolated PMV. Using this procedure we obtained three plasma membrane vesicles populations: (1) X-enriched sperm plasma membrane vesicles (PMV-X) (approximately 68% X-sperm); (2) Y-enriched plasma membrane vesicles (PMV-Y) (approximately 72% Y-sperm); and (3) non-enriched plasma membrane vesicles (PMV-X/Y) (approximately equal amounts of X- and Y-sperm). The pelleted material resulting after centrifugation of X- and Y-enriched sperm subpopulations is the X- and Y-enriched non-membrane sperm component.

One may use enriched PMV and enriched non-membrane sperm component to identify an array of sex-associated molecules which exist predominately in X-or Y-sperm. This includes X- and Y-SAM proteins and other SAM molecules (such as lipids and carbohydrates), and X- and Y-non-membrane sex-associated molecules (such as cytoplasmic proteins or other molecules). One identifies these molecules using techniques analogous to the ones we describe for identifying SAM proteins.

EXAMPLE III

Identification of SAM

Proteins on 1-D Gels

We used PMV-X and PMV-Y of Example II to identify X-SAM and Y-SAM proteins on 1-D gels. We began by solubilizing PMV-X and PMV-Y in 2% SDS and $^{125}$I labelled using chloramine-T (Stanley et al., 1971; Frost, 1977). We separated the proteins by Laemmli SDS/PAGE (5%–15% T; 5% C). For comparison we loaded three lanes on a single gel with PMV-X, PMV-Y, and molecular weight standards, respectively. We conducted the electrophoresis at 100 V constant through the stacking gel/125 V constant through the separation gel with water cooling.

We compared autoradiographs (after 1 week) of the X- and Y-profiles by observing a band on one profile and comparing it with the corresponding location on the other profiles, looking for an increase or decrease in density. When the density of a band in the X-profile was increased in comparison to the Y-profile, we designated that band an X-SAM protein. If the band was increased in density on the Y-profile and decreased in density on the X-profile, then we designated it a Y-SAM protein. As an internal control we also compared the density of bands to the density of the corresponding bands on the X/Y profile (prepared from PMV-X/Y.) This band should be intermediate in density as compared to the bands of the X- and Y-SAM proteins. We then compared protein bands designated SAM on autoradiographs with the molecular weight standards in order to approximate the molecular weight of the identified SAM proteins.

We ran similar comparative gels using silver staining to identify the various proteins. Again, by comparison among the X-, Y- and X/Y profiles we identified the SAM proteins of this invention. In comparing various gels of separated proteins of PMV-X, PMV-Y and PMV-XY, the molecular weight standards are important. The molecular standards are aligned such that each standard overlaps with the corresponding molecular weight standard on the other gel. With this base for comparison, one may obtain a visual identification of the desired SAM proteins by location, color, and staining density relative to other bands on a gel profile.

Because of this ability to compare gels, once the X- and Y-SAM proteins of this invention are identified on a gel of membrane proteins from enriched sperm subpopulations, one may use those molecular weight locations to identify the X- and Y-SAM proteins on gels of plasma membrane proteins from whole (non-enriched) sperm.

An important attribute of this invention is that cell sorting and component enrichment need only be done once, to originally identify specific SAM proteins. Subsequently, one may use the gel characteristics of the SAM proteins themselves to identify and to isolate large amounts of those proteins for further study and use.

One may then isolate SAM proteins from the PMV-X and PMV-Y by one of the following methods. In the first method, SDS/PAGE profiles (Laemmli, 1970) of PMV-X and PMV-Y are run side-by-side and silver stained (Wray et al., 1981). In the second method, solubilized X- and Y plasma- membrane proteins are iodinated with $^{125}I$ using chloramine-T (Stanley and Haslam, 1971) and a similar SDS/PAGE profile is run and autoradiographs of the separated proteins are obtained. In either case we isolated the SAM proteins as described in Example IV.

EXAMPLE IV

Bull SAM Proteins Identified by 1-D Gels

We identified bands in 1-D gels which contain SAM proteins from bull sperm. We processed bull sperm as previously described, separated the proteins from X- and Y-enriched sperm plasma membrane vesicles by SDS/PAGE, and determined the molecular weights of bands of increased density on one as opposed to the other. We found bands containing X-SAMs of the following molecular weights: 19 kD, 25 kD, 29 kD, 32 kD, 39 kD, 72 kD, and 120 kD. We found bands containing Y-SAMs of the following molecular weights: 15 kD, 45 kD, 57 kD, 64 kD, and 125 kD.

Although this method accurately identifies bands containing SAM proteins, and one can isolate defined SAM proteins by cutting-out the bands on these gels, this is not the preferred method for precisely measuring the molecular weights of SAM proteins. This system has a MW standard deviation of 4.2% and some bands may contain more than one SAM protein of slightly different molecular weight.

Nevertheless, for the purposes of the present invention, it is not essential to determine whether the SAM bands identified only by molecular weight (Example III) contain only one protein. Without making any further separation or characterization of the proteins of a given band, one can use the bands, which contain refined SAM proteins, directly to prepare antibodies (either polyclonal or monoclonal) which will bind selectively to X- or Y-sperm. One can employ these antibodies in the methods and compositions of this invention for increasing the probability that offspring will be of a desired sex. The procedures which are used are described below.

EXAMPLE V

Identification Of SAM Proteins By 2-D Gels

Although the SDS/PAGE gels described in Example III permit the identification of the SAM proteins of this invention and a characterization of those proteins by molecular weight, it is preferable to use two dimensional IPG-SDS/PAGE gels to identify and characterize SAM proteins and to isolate substantially pure SAM proteins. Two-dimensional gel analysis is a process in which proteins are separated first in one dimension by their net electrical charge (pI) and next in a second dimension by their molecular weight. We performed 2-D gel electrophoresis of plasma membrane proteins from X- and Y-enriched sperm subpopulations and from non-enriched sperm produced X-, Y- and X/Y profiles, respectively.

We purchased equipment for horizontal isoelectric focusing, including casting molds, rehydration cassettes, Immobilines ® (acrylamide derivatives) pK 3.6, 4.6, 6.2, 7.0, 8.5, 9.3, LKB ampholine (carrier ampholyte) 3.5–10, and gel bond PAG film from LKB. We purchased additional carrier ampholyte (3–10) from Pharmacia and Serra. We purchased acrylamide from Amresco; bis from FMC; SDS from BDH; urea from Schwarz/Mann. We purchased all other chemicals from Sigma.

In a preferred 2-D gel separation process of this invention, we began with solubilized plasma membrane vesicles from whole sperm and from X- and Y-enriched sperm subpopulations isolated as in Example II. The LKB 2117 Multiphor II Electrophoresis System laboratory manual gives instructions and formulations for pouring 5.0% T, 2.7% C, 0.5 mm thick IPG gels with a broad range pH gradient of 4–10. We allowed gel polymerization to proceed for 1 hour in an oven heated to 50° C. Following polymerization, we removed gels from the mold, washed them twice for 30 minutes in HPLC water and then rinsed them for 30 minutes in a solution of 2.5% glycerol. We air-dried the gels overnight in a dust free cabinet. Prior to focusing, we rehydrated IPG gels with a solution consisting of 8M urea, 10 mM dithiothreitol (DTT), 0.5% (volume/volume) nonidet p-40 (NP-40), 0.5% carrier ampholyte (CA). We utilized different brands of carrier ampholyte (LKB ampholines, Pharmalyte ®, and Servalyte ® 3–10) to insure the best possible pH distribution. It is important that the carrier ampholyte used span the entire pI range over which the sample is to be focused. We included carrier ampholyte in rehydration of the gel in order to decrease hydrophobic interaction with basic immobilines.

We solubilized bull plasma membrane proteins with a solution containing 9M urea, 2% (weight/volume) DTT, 2% (volume/volume) NP-40, 0.8% (volume/volume) carrier ampholyte. To aid in solubilization, we sonicated samples in a water bath sonicator at 4° C. for 10 minutes. We pelleted remaining aggregates by centrifugation at 13,000×g for 10 minutes.

We loaded the solubilized samples in preformed wells near the anode. Anolyte and catholyte were 10 mM phosphoric acid and 10 mM sodium hydroxide respectively. Focusing parameters were 170 volts, 2 mA, and 5 W until 1000 volt hours, followed by gel dependent increases to 1700 volts for a total of 7000 volt hours. Lower starting voltage improved protein entry. The pH gradient was measured in 1 cm increments with a calibrated LKB pH surface electrode immediately following run.

Following isoelectric focusing, we cut the gel into strips corresponding with sample wells. We incubated the strips in equilibration buffer and loaded them directly onto SDS slab gels. We equilibrated for 30 minutes with gentle shaking at room temperature in 8 ml of a solution containing 0.05M tris-HCl pH 6.8, 6M urea, 2% (weight/volume) SDS, 1% (weight/volume) DTT, 30% glycerol and 0.001% bromphenol blue. Following equilibration we rinsed the gel strips briefly to remove excess equilibration buffer and loaded them directly onto vertical 11.0% T, 2.7% C, 1.5 mm thick SDS slab gels with a stacker of 4.8% T, 2.7% C. We electrophoresed proteins at 100 volts until the dye front moved through the stacker. We then increased the voltage to 140 volts for the remainder of the run.

Upon staining, these 2-D gels produced hundreds of spots. Using internal standards, we determined the molecular weight and pI of these spots. We measured the integrated intensity of the gel spots using a BioImage scanner (Kodak). We determined the mean integrated intensity of the spots from about thirty X/Y profiles and from about three X- and three Y-profiles. Then we calculated for each protein spot the difference in the mean integrated intensity on the X-profiles and the mean integrated intensity on the Y-profiles. We designated a protein as a SAM protein when this difference was at least 1.8 standard deviations from the mean integrated intensity of the protein on the X/Y profiles. X-SAM proteins were, of course, more intense on X-profiles, and Y-SAM proteins, on Y-profiles. The SAM proteins we identified are presented in Table 1. The molecular weights are accurate to within 4.2% and the isoelectric points, to within ±0.16 pH. We do not intend this list to exhaust the entire class of SAM proteins—more, undoubtedly, exist. For example, our examination of the 2-D gels revealed many spots which appeared on one profile but not on the other. In some cases, the absence of a spot indicates a protein whose intensity is below the range of sensitivity for detection. Clearly, one of ordinary skill in the art could visualize these proteins by loading more sample on the gel or by using more sensitive staining techniques. Then, using the techniques advanced in this invention, one could identify which among these are SAM proteins.

TABLE I

| X-SAM | | Y-SAM | |
|---|---|---|---|
| MW(kD) | pI | MW(kD) | pI |
| 20.9 | 5.74 | 9.6 | 6.52 |
| 26.3 | 7.58 | 19.9 | 5.67 |
| 27.8 | 6.08 | 29.0 | 6.67 |
| 44.1 | 6.90 | 30.3 | 5.77 |
| 52.5 | 5.33 | 36.5 | 7.16 |
| 58.0 | 5.99 | 41.1 | 6.21 |
| 59.4 | 6.59 | 55.5 | 6.82 |
| 59.5 | 6.81 | 55.9 | 5.25 |
| 62.1 | 7.23 | 58.0 | 8.67 |
| 62.5 | 5.54 | 62.9 | 6.34 |
| 62.7 | 6.85 | | |
| 62.8 | 6.64 | | |
| 63.9 | 5.83 | | |
| 68.2 | 5.95 | | |
| 78.6 | 7.14 | | |

EXAMPLE VI

The H-Y Antigen Is not a SAM Protein

To determine whether or not the H-Y antigen, previously asserted to be sex associated, is a SAM protein, we isolated whole sperm plasma-membrane proteins and separated them as described on 2-D gels. Then we performed an immunoblot as described in Example IX using anti-H-Y monoclonal antibodies which Dr. G. C. Koo generously supplied to us. The blot revealed eight proteins having an epitope recognized by anti-H-Y monoclonal antibody. We determined the molecular weights and pI for these proteins and present them in Table II. Significantly, none of these proteins matches any of those we identified as SAM proteins in Table I. Therefore, the H-Y antigen is not a sex-associated membrane protein as defined in this invention.

TABLE II

| H-Y Antigen* | |
|---|---|
| MW(kD) | pI |
| 23.4 | 6.96 |
| 39.5 | 5.89 |
| 34.8 | 5.96 |
| 42.6 | 6.80 |
| 38.4 | 6.96 |
| 41.6 | 7.58 |
| 57.5 | 6.00 |
| 56.1 | 5.91 |

*Bull sperm plasma-membrane proteins separated by 2-D gel which bound anti-H-Y monoclonal antibody in immunoblot.

EXAMPLE VII

Use Of Gel Profiles

Larger amounts of the SAM proteins of this invention one are obtained by isolating the proteins from whole sperm.

In one embodiment of that process, we prepared one-dimensional SDS/PAGE gels of PMV-X, PMV-Y, and PMV-XY as described in Example III. (Alternatively, a two-dimensional gel as described in Example IV is used.) We then transferred the protein bands from the PMV-X/Y gel to a set of sheets of nitrocellulose (NC) by transblotting. In this technique, one positions the gels and NC sheets adjacent to one another, and applies a constant electric current to transfer all of the protein bands on the gels to the NC sheets, maintaining their relative positions. In one embodiment of our invention, we performed the transfer using SDS/PAGE 1D gels in the presence of 25 mN Tris, 192 mN glycine, and 20% methanol (Towbin et al., 1979) using 250 mA of constant current for about 16 hours at 4° C.

Following the transfer to NC, we stained the bands with 0.5% amido black in 7% acetic acid. (The technique of using amido black is described by Schaffner et al. (1973), and this stain is available commercially from Sigma Chemical Co., St. Louis, Mo.) We prefer to use amido black stain because it does not interfere with the subsequent preparation of anti-sera or hybridomas from proteins.

In the embodiment of this invention using the 1D SDS/PAGE gels, to identify the SAM protein bands on the NC sheets for use in immunizing animals, we aligned silver stained profiles of the SDS/PAGE gel of molecular weight separated SAM proteins as described in Example III (with molecular weight standards) with the molecular weight standards on the amido black stained transblotted SDS/PAGE 1D profiles. The alignment of the molecular weight standards allows the matching of the silver stained SAM bands on the SDS/PAGE gel with the corresponding amido black stained protein bands on the NC sheets. We then cut out the amido black stained bands on the NC sheets that correspond to SAM proteins using a razor blade.

We used the cutout bands to isolate the desired SAM proteins or to prepare directly antibodies to these proteins. For example, in one embodiment the cutout bands are surgically implanted to raise antibodies. Alternatively, the proteins in those bands are extracted with a suitable solvent, such as dimethylsulfoxide (DMSO) and injected the into a test animal. We prefer the latter procedure. In such an extraction, we prefer to extract the NC band with 100 $\mu$l DMSO. We then mixed the resulting DMSO solution with 1 ml of adjuvant (Freund's complete) prior to injection to raise antibodies. (The preferred embodiment is 100 $\mu$l of adjuvant.)

There is now available to the art means to isolate the binding portion of the immunoglobulin molecule. One example is a kit to isolate Fab or F(ab')$_2$ fragments, available from Pierce Corporation, Rockford, Ill. When we refer to antibodies in this specification, we therefore mean to include fragments such as those which contain only the binding portion.

EXAMPLE VIII

Hybridomas And Monoclonal Antibodies

We prepared several hundred hybridomas using 150 pooled NC strips, prepared as described above, which bracketed the 19,000 and 25,000 dalton K-SAM bands and the 57,000 and 64,000 dalton Y-SAM bands, respectively ($\pm$5%) (bull sperm).

For hybridoma production, we used a non-secreting Balb/c mouse line SP2/0-AG14 obtained from the American Type Culture Collection, Rockville, Md. We used ATCC CAT1581-CRL (batch F-5286) as our myeloma line. We grew cells in 10% FCS/DMEM or RPMI-1640 (we prefer the latter) and maintained between 0.2-1.0$\times$10$^6$ cells/ml.

We immunized mice using the SAM/DMSO/adjuvant mixture described in Example VII. Between 20 $\mu$g and 200 $\mu$g of protein was used per mouse. Two weeks later and four days prior to the collection of spleens and fusion, we injected subcutaneously a boost of 100-150 $\mu$g of PMV-X/Y or 1$\times$10$^7$ whole sperm in PBS to stimulate X or Y specific clones that produce antibodies to the native SAM protein configuration. (We prefer IP injection of whole sperm.) It should, of course, be understood that one may use other protocols to immunize the mice. For example, the mice could be treated as above with the SAM/DMSO/Freund's complete adjuvant mixture, described above, boosted once per day for 4 days with PMV-XY in PBS, and the spleens collected.

One day prior to fusion, myeloma cells were split to ensure that they were in log phase growth. On the day of fusion, the animal was sacrificed and splenectomized. We rinsed the spleen in sterile DMEM or RPMI-1640 (we prefer the latter) and teased it to separate splenocytes. (We now separate using syringe and needle perfusion.) Typical cell recovery from 1 spleen was 1$\times$10$^8$ cells. We washed splenocytes 3 times in DMEM or RPMI 1640. We prefer the latter.) The myeloma cells were also washed 3 times. We counted splenocytes and myeloma cells and mixed them together at a ratio of 7 spleen cells:1 myeloma cell. (We currently use 1:1.) We then centrifuged the cells at 1000 rpm (Mistral 3000) and decanted the supernatant.

Fusion was done with 1 ml of PEG for a period of one minute with gentle agitation. (We currently adjust PEG to pH 7.) We stopped the reaction with 20 ml DMEM (or preferably RPMI 1640) and centrifuged the mixture as before. We decanted the DMEM (or preferably RPMI 1640) and gently resuspended the pellet of fused cells in 12 ml of HAT (hypoxanthine aminopterin thymidine) medium and plated the cells into twenty-four well plates (1 ml of cell suspension/well). (We currently use HMT—hypoxanthine methotrexate thymidine.) We incubated plates overnight in a 7% CO$_2$ incubator at 37° C. The next day we fed the wells an additional ml of HAT (or HMT) medium and left them to incubate for 7 to 14 days. We removed the HAT (HMT) medium and replaced it with 10% FCS/DMEM or RPMI. (We prefer the latter.) We incubated plates until colony formation was visible. After the colonies had expanded into larger cultures, we froze them at $-$70° C. and stored them long-term in liquid nitrogen.

(1) ELISA Assay

We screened supernatants by an ELISA assay as follows: 96-well microplates were coated with 100 $\mu$l of PMV-X/Y (2 $\mu$g/ml) in 0.05M carbonate-bicarbonate buffer (pH 9.6) for 16-18 h at 4° C. in a humid chamber (or for 2-4 h in a 37° C. incubator). The carbonate-antigen solution may be used 2-3 times for blocking plates (which may then be stored for subsequent use at $-$20° C.). We incubated the plates for 30 min at room temperature, added 1$\times$10$^5$ sperm cells per well and incubated the wells at 4° C. overnight in the humid chamber. (We prefer whole cells as antigens.)

We washed the plates with 200 $\mu$l of 0.05% Tween 20 in 0.02M phosphate saline buffer (pH 7.2) three times at room temp. The wells may be filled with 200 $\mu$l of 3.0% gelatin in PBS-Tween, incubated for 30 min at room temperature in a humid chamber, and the blocking solution (gelatin-PBS) aspirated-off. However, preferably we omitted these steps and instead immediately incubated the plates with 100 $\mu$l of normal (from either a non-immunized mouse or media as above—a negative control) and immune supernatants (undiluted) at 37° for 1 hour, in a humid chamber, and then wash the plates as above. Next, 100 $\mu$l of peroxidase conjugated goat anti-mouse IgG in the appropriate dilution in 0.5% PBS/tween 20 was added to each well and incubated for 1 h at 37° in a humid chamber and the plates washed as before. We added 100 $\mu$l of a 1:2 mixture of TMB(3,3',5,5'tetramethylbenzadine)/H$_2$O$_2$ to each well and incubated the plates for 60 min at room temperature. We determined color development visually or determined absorbance at 660 nm using a Beckman Biomek 1000 robotic arm.

In these assays, we have assumed that the ratio of the absorbance reading of a highly positive sample to that of a negative sample in indirect ELISA should be at least 5:1. We also considered as positives all wells with results greater than 3 standard deviations from the mean of the negative controls.

We cloned positive cell lines by limiting dilutions of 1 cell/well and 3 cells/well. We expanded each well by moving the contents of the well to a larger well and finally to a flask. We stopped such expansion at a 150 cm$^2$ sized flask.

EXAMPLE IX

Immunoblots Of SAM Proteins And Monoclonal Antibodies

We analyzed monoclonal antibodies produced from those hybridomas that were positive in the ELISA assay produced above for binding activity against the X-SAM and Y-SAM proteins of this invention.

We washed the nitrocellulose sheets carrying the SDS/PAGE protein bands, described above, three times (5 min/wash) in a washing solution (20 mN Tris-HCl (pH 8.2), 20 mN sodium azide, 0.9% NaCl and 0.1% BSA). (We now prefer 0.8% NaCl, 0.02% $N_2PO_4$, 0.144% $Na_2PO_4.H_2O$, 10 mN sodium azide, and 0.1% BSA). They were then blocked by incubation with the washing solution augmented with 4.9% BSA to a final BSA concentration of 5% and shaking for 45 min. Alternatively, we blocked overnight at 4° C. After washing 3 times as before, we placed the NC blots in a miniblotter. We then applied the monoclonal antibodies (mAbs) to the nitrocellulose blots. For a 25 μg transblot, we diluted mAb supernatants 10 times with the washing solution, augmented with 1% normal or total goat-serum. We pipetted 130 μl of the diluted mAb supernatants in duplicate into the apparatus. As a negative control we used diluted washing solution lanes in duplicate. As a positive control we used antibodies that bound to greater than 90% of all sperm. We incubated the blots with the mAbs or the positive and negative controls for 30 minutes and then washed them several times to ensure removal of all unbound antibody.

Following washing, we added 130 μl Auroprobe BL+ stain (Janseen) to all of the lanes and incubated them for at least 2.5 h (incubation for 5 h is also permissible). We washed the lanes several times (3 min/wash) with washing solution, removing the liquid with the vacuum manifold.

We placed the blot in a clean dish, washed again with distilled water and incubated the blot with Intense II silver stain (Janseen) (about 70 ml) for 10 min. We rinsed 3 times with distilled water (5min/rinse). (We now prefer 15-40 min rinse.) Results were positive when color density was greater than negative control.

We found that these monoclonals bound to 1-D gels at molecular weight regions corresponding to SAM proteins identified in Example IV.

EXAMPLE X

Modification of Semen

Polyclonal or monoclonal antibodies of this invention are useful to modify mammalian semen to increase the percentage of male or female offspring resulting from fertilization by the modified semen. Antibodies binding to X- or Y-SAM proteins of this invention, as described above, when incubated with a semen sample, bind to X- and Y-sperm, respectively. Sperm that are bound with antibodies become inactivated—their mobility is impeded and they become ineffective at fertilizing an ovum. For assured effectiveness, the antibody preparation is preferably produced from the sperm of the same mammalian species with which it is to be used. However, one can expect sex-selective cross-reactions to occur for sperm of other animals. Consequently, our antibody preparations are useful for modifying sperm of more than one species of animal.

It will be clear that in any of the methods we describe immunogenic fragments of the SAM proteins or other proteins which induce antibodies cross-reactive with SAM proteins are useful for immunization.

We added an antibody that had been raised to a SAM protein (100–500 ug per million sperm) to neat semen. The semen was either collected and frozen in liquid nitrogen, or it may be freshly ejaculated. The antibodies were preferably in a physiologically acceptable carrier formulated to have the properties of maintaining the activity of the antibodies, being non-toxic to sperm, and conducive to binding of the antibodies to the sperm. For example, we employed a sterile, buffered aqueous carrier which had a physiologically acceptable pH and salt content. The carrier had a pH from 6.4 to 8.4 and contain a phosphate buffer. A unit dose form of such a preparation should contain sufficient antibodies, for example, to preferentially deactivate all of the X-bearing or Y-bearing sperm in an artificial insemination dose of semen. Antibodies are best stored lyophilized.

Preferably, the antibodies are incubated with the semen sample for 15–60 min at 37° C. Following incubation, the mixture is used directly for artificial insemination (AI) or is frozen in liquid nitrogen according to standard procedures for later use. The antibodies can be added at any time during the course of processing a semen sample. The important steps are: (1) the antibody is given adequate time to bind to sperm; and (2) the antibody to sperm ratio is set such that there is excess antibody. Using either monoclonal or polyclonal antibodies, the important factors are incubation time and antibody to sperm ratio. In one embodiment the incubation is carried out in vivo, such as by simultaneously introducing the semen and the antibody preparation (preferably premixed with the semen) into the vagina of the female mammal. Alternatively, the antibodies are added to the petri dish during in vitro fertilization.

In a preferred method of artificial insemination, monoclonal antibodies are mixed with freshly ejaculated semen in such proportions to give excess monoclonal antibody (i.e., unbound to sperm). The combination of fresh semen with monoclonal antibody is then mixed with cryopreservatives and packaged in straws in the then usual fashion (industrial standards). The straws are used in the usual methods for artifically inseminating cattle.

EXAMPLE XI

Monoclonal Antibody Binding To Whole Sperm

We bound monoclonal antibodies to whole sperm by the following preferred method: We thawed antibody supernatants in a 37° C. bath and diluted with a combination of Dulbecco's/PBS, Hoechst stain, and BSA as previously described. We diluted a whole sperm sample with a labeling solution to a final concentration of $480 \times 10^6$ sperm cells per 12 mls. We added monoclonal antibody (ca. 200 μl supernatant) to $1 \times 10^6$ cells and allowed it to incubate for 1 hour at room temperature. We centrifuged the cells at 100×g for 5 minutes, discarded the supernatant and resuspended the cell pellet in 200 μl of a 1:20 dilution of an affinity-purified anti-mouse antibody conjugated with R-Phycoerythrin. Following a second centrifugation, we discarded the supernatant and resuspended the cell mixture in a 10% neutral buffered formalin solution.

EXAMPLE XII

Other Uses of SAM Proteins

SAM proteins are also useful in vivo to influence the sex of the offspring. In one illustrative method, a female mammal is immunized with a SAM protein preparation. The immunization is carried out so that it is effective to generate polyclonal antibodies, which will be present in the reproductive fluid of the female mammal for selective binding to X-SAM or Y-SAM when semen is introduced into the vagina. Immunization is as previously described with the site of immunization being that which produces antibodies that are sex specific. The animal is then allowed to mate naturally.

The proteins are also useful to decrease fertility by immunizing a female as just described with both X- and Y-SAM proteins.

The SAM proteins of this invention are also useful to detect the presence of anti-SAM antibodies in a sample. The presence of antibodies in a serum sample might explain infertility or the unusual proclivity to produce offspring of a certain sex. One might test a sample by performing an ELISA assay such as in Example VIII using SAM proteins rather than PMV as the substrate.

EXAMPLE XIII

Other Uses of Antibody Preparations

The antibody preparations of this invention are useful for other purposes besides modifications of semen to increase the percentage of male or female offspring. For example, the sex specific antibodies of this invention are useful in an affinity column to extract quantities of SAM proteins from a mixture of substances. If the substances and SAM protein are contained in a lipid microdomain then those substances that are associated with that protein can also be enriched. In the embryo transplant industry, those SAM proteins that migrate or are found in the fertilized egg may be identified using labeled antibodies that have been raised to SAM proteins, thereby sexing the embryo. Should those SAM antigens, associated with the fertilized egg, escape into the maternal system, incubating maternal body fluids with labeled anti-SAM protein antibodies, or using SAM proteins or determinants thereof, will allow for prenatal sex and pregnancy determination.

Antibody preparations of this invention can also be used for identifying plasma membrane proteins associated with either the X-chromosome or Y-chromosome. In still another use, the antibodies are useful for identifying non-sperm polypeptides or proteins which exhibit antigenic properties capable of generating antibodies which bind selectively to Y-sperm or X-sperm. In a related use, the antibodies are useful for isolating those polypeptides or proteins. Another related use is that of utilizing antibodies raised to Y-SAM proteins or to X-SAM proteins for isolating polypeptides or proteins that are associated in the microdomain of the proteins that bind to these antibody preparations.

EXAMPLE XIV

Sex-Chromosome Linked Traits

The SAM proteins of this invention are also useful for increasing or decreasing the probability that offspring will carry a gene for a particular sex-chromosome linked trait. Sex-chromosome linked traits are genetic characteristics determined or controlled by genes on either the X-or Y-chromosome that therefore show a different pattern of inheritance in males and females. For example, in humans, color blindness and hemophilia are X-chromosome linked traits.

We have already described how to use SAM proteins to produce antibodies which bind to sperm carrying a particular sex chromosome. Because these antibodies inactivate sperm according to the sex chromosome they carry, they are also useful for inactivating sperm carrying a gene for a particular sex-chromosome linked trait. For example, if one wished to decrease the probability that offspring carry a gene for a particular X-chromosome linked trait, one would incubate the semen sample with antibodies binding to X-SAM proteins. This would inactivate the X-sperm carrying the undesirable gene. Conversely, if one wished to increase the probability that offspring carried a particular gene for a X-chromosome linked trait, one would incubate a semen sample with antibodies binding to Y-SAM proteins. This would inactivate Y-sperm, leaving viable the X-sperm which carried the desirable gene. Likewise, the corresponding procedures are used for genes for Y-chromosome linked traits.

While we have hereinbefore described a number of embodiments of this invention, it is apparent that one of skill in the art could alter our procedures to provide other embodiments which utilize the processes and compositions of this invention.

Therefore one will appreciate that the scope of this invention is to be defined by the claims appended hereto rather than the specific embodiments which we have presented by way of example.

Publications

N. J. Alexander and D. J. Anderson, "Immunology of Semen", *Fert. and Steril.*, 47, pp. 192–205 (1987)

G. F. Ames and K. Nikaido, "Two-Dimensional Gel Electrophoresis Of Membrane Proteins", *Biochem.* 15, pp. 616–23 (1976)

G. B. Anderson, "Identification Of Embryonic Sex By Detection of H-Y Antigen", *Theriog.*, 27, pp. 81–97 (1987)

D. Bennett and E. Boyse, "Sex Ratio In Progeny Of Mice Inseminated With Sperm Treated With H-Y Antiserum", *Nature*, 246, pp. 308–09 (1973)

D. Bennett and R. S. Johnson, "Biotech Experts Report Progress In Agricultural Research", in Genetic Engineering News, September (1985)

R. E. Billingham and W. K. Silvers, "Induction Of Tolerance Of Skin Isografts From Male Donors In Female Mice", *Science*, 128, pp. 780–81 (1958) ("Billingham-I")

R. E. Billingham et al. "A Second Study On The H-Y Transplantation Antigen In Mice", *Proc. Royal Society of London, Series B, Biological Sciences*, 163, pp. 61–89 (1965) ("Billingham-II")

H. von Boehmer "Fine Specificity Of A Continuously Growing Killer Cell Clone Specific For H-Y Antigen", *Eur. J. Immunol.*, 9, pp. 592–97 (1979)

E. A. Boyse and D. Bennett, "Differentiation And The Cell Surface; Illustrations From Work With T Cells And Sperm", in *Cellular Selection and Regulation In The Immune Response*, G. M. Edelman ed., Raven Press, New York, pp. 155–76 (1974)

F. Bradley et al., "Structural Proteins Of The Mouse Spermatozoan Tail: An Electrophoretic Analysis", *Biol. Reprod.*, 24, pp. 691–701 (1981)

M. P. Bradley and B. F. Weslop, "A Biochemical And Immunological Approach To The Identification Of H-Y Antigenic Proteins Secreted From Daudi Cells", *Hum. Genet.*, 71, pp. 117–21, (1985)

B. F. Brandriff et al., "Sex Chromosome Ratios Determined By Karyotypic Analysis In Albumin-Isolated Human Sperm", *Fertil. Steril.*, 46, pp. 678–85 (1966)

M. Brunner et al., "On The Secretion Of H-Y Antigen", *Cell*, 37, pp. 615–19 (1984)

D. N. Crichton and B. B. Cohen, "Analysis Of The Murine Sperm Surface With Monoclonal Antibodies", *J. Reprod. Fert.*, 68, pp. 497–505 (1983)

W. P. Dmowski et al., "Use Of Albumin Gradients For X and Y Sperm Separation And Clinical Experience With Male Sex Preselection", *Fertil. Steril.*, 31, pp. 52–57 (1979)

E. M. Eddy and J. K. Koehler, "Restricted Domains Of The Sperm Surface" in *Scanning Electron Microscopy*, Sem. Inc. AMF O'Hare, Ill. pp. 1313–23 (1982)

R. J. Ericsson et al., "Isolation Of Fractions Rich In Human Y Sperm", *Nature*, 246, pp. 421–24 (1983) H. J. Evans, "Properties of Human X and Y Sperm", *Proc. Int. Symp. Gen. Sperm.*, pp. 144–59 (1972)

D. L. Garner et al., "Quantification Of The X- and Y-Chromosome-Bearing Spermatozoa of Domestic Animals By Flow Cytometry", *Biol. Repro.*, 28. pp. 312–21 (1983) ("Garner-I")

D. L. Garner et al., "An Overview of Separation of X- and Y-Spermatozoa", *Proceedings of the Tenth Technical Conference on Artificial Insemination and Reproduction and Inseminator Training, Miniconference*, pp. 81–85 ("Garner-II")

G. Gillis et al., "Isolation And Characterization Of Membrane Vesicles From Human And Boar Spermatozoa: Methods Using Nitrogen Cavitation And Ionophore Induced Vesiculation", *Prep. Bioch.*, 8, pp. 363–78 (1978)

B. Gledhill, "Cytometry Of Mammalian Sperm", *Gamete Research*, 12, pp. 423–38 (1985)

E. H. Goldberg et al., "Serological Demonstration Of H-Y (Male) Antigen On Mouse Sperm", *Nature*, 232, pp. 478–80 (1971) ("Goldberg-I")

E. Goldberg, "Current Status Of Research On Sperm Antigens: Potential Applications As Contraceptive Vaccines", *Res Front Fert Reg.*, 2 pp. 1–11 (1983) ("Goldberg-II")

Hafs and Boyd, "Sex Ratio at Birth—Prospects for Control" *Am. Soc. Anim. Sci.* pp. 85–97 (1971)

J. I. Hall and S. S. Wachtel, "Primary Sex Determination: Genetics And Biochemistry", *Mol. Cell. Biochem.*, 33, pp. 49–66 (1980)

T. S. Hauschka and B. A. Holdridge, "A Cytogenetic Approach To The Y-Linked Histocompatibility Antigen Of Mice", *Ann. N.Y. Acad. Sci.*, 101, pp. 12–23 (1962)

U. Hegde et al., "Phytohaemagglutinin As A Molecular Probe To Study The Membrane Constituents Of Human X-And Y-Bearing Spermatozoa", *J. Rep. Immun.*, 2, pp. 351–57 (1981)

A. C. Hinrichsen-Kohane, "Analysis Of Antigen Expression On Muman Spermatozoa By Means Of Monoclonal Antibodies", *Fertil. Steril.*, 43, pp. 279–85 (1985)

P. Hoppe and G. C. Koo, "Reacting Mouse Sperm With Monoclonal H-Y Antibodies Does Not Influence Sex Ratio Of Eggs Fertilized In Vitro", *J. Rep. Immun.*, 6, pp. 1–9 (1984)

E. N. Hughes and J. T. August, "Characterization Of Plasma Membrane Proteins Identified By Monoclonal Antibodies", *J. Biol. Chem.*, 256, pp. 664–71 (1981)

L. A. Johnson and D. Pinkel, "Modification Of A Laser-Based Flow Cytometer For High Resolution DNA Analysis Of Mammalian Spermatozoa", *Cytom.*, 7, pp. 268–73 (1986)

D. J. Arndt-Jovin and T. Jovin, "Analysis And Sorting Of Living Cells According To Deoxyribonucleic Acid Content", *J. Histochem. Cytochem.*, 25, pp. 585–89 (1977)

G. C. Koo et al., "Expression Of H-Y Antigen During Spermatogensis", *Immunogen.* 9, pp. 293–96 (1979) ("Koo-I")

G. C. Koo et al., "Topographical Loacation Of H-Y Antigen On Mouse Spermatozoa By Immunoelectronmicroscopy", *Proc. Nat. Acad. Sci.*, 70, pp. 1502–05 (1973) ("Koo-II")

G. C. Koo and A. Varano, "Inhibition Of H-Y Cell-Mediated Cytolysis By Monoclonal H-Y Specific Antibody", *Immunogen.* 14, pp. 183–88 (1981) ("Koo III")

G. C. Koo and C. Goldberg, "A Simplified Technique For H-Y Typing", *J. Immunol. Methods*, pp. 197–201 (1978) ("Koo IV")

R. Gore-Langton et al., "The Absence Of Specific Interactions Of Sertoli-Cell-Secreted Proteins With Antibodies Directed Against H-Y Antigen", *Cell*, 42, pp. 289–301 (1983)

C. Gregory-Lee et al., "Monoclonal Antibodies To Buman Sperm Antigens", *J. Repr. Immun.*, 4, pp. 173–81 (1982)

C. A. Lingwood et al., "The Preparation of Rabbit Antiserum Specific for Mammalian Testicular Sulfogalactoglycerolipid", *J. Immunol.*, 124, pp. 769–774 (1980) ("Lingwood-I")

C. Lingwood et al., "Tissue Distribution of Sulfolipids in the Rat. Restricted Location of Sulfatoxygalactosylacylalkylglycerol", *Can. J. Biochem.*, 59, pp. 556–563 (1981) ("Lingwood-II")

C. Lingwood and H. Schachter, "Localization of Sulfatoxygalactosylacylalkylglycerol at the Surface of Rat Testicular Germinal Cells by Immunocytochemical Techniques: pH Dependence of a Nonimmunological Reaction Between Immunoglobulin and Germinal Cells", *J. Cell Biol.*, 89, pp. 621–630 (1981) ("Lingwood-III")

R. McCormick et al., "Sex Preselection In The Rabbit Via Immunological Or Immunosedimentation Techniques", *Infert.* 5, pp. 217–27 (1982)

D. H. Moore, II and B. L. Gledhill, "How Large Should My Study Be so That I Can Detect an Altered Sex Ratio?", *Fert. and Steril.*, 50, pp. 21–25 (1988)

G. P. Moore, "DNA-Dependent RNA Synthesis In Fixed Cells During Spermatogenesis In Mouse", *Exptl. Cell Res.*, 68, pp. 462–65 (1971)

J. M. Morrell et al., "Sexing of Sperm by Flow Cytometry", *Vet. Record.*, 122, pp. 322–324 (1988)

Y. Nagai et al., "Testis-Organizing H-Y Antigen Of Man May Lose Its Receptor Binding Activity While Retaining Antigenic Determinants", in *Testicular Development, Structure and Function*, ed. A. Steinberger and E. Steinberger, Raven Press, New York, pp. 41–46 (1980) ("Nagai-I")

Y. Nagai et al., "The Identification Of Human H-Y Antigen And Testicular Transformation Induced By Its Interaction With The Receptor Site Of Bovine Fetal Ovarian Cells", *Differen.*, 13, pp. 155–64 (1979) ("Nagai-II")

T. Noland et al., "Purification And Partial Characterization Of Plasma Membranes From Bovine Spermatozoa", *Biol. Reprod.*, 29, pp. 987–98 (1983) ("Noland-I")

T. Noland et al., "Protein Phosphorylation Of Plasma Membranes From Bovine Epididymal Spermatozoa", *Biol. Reprod.*, 31, pp. 185–94 (1984) ("Noland-II")

D. A. O'Brien and A. R. Bellve, "Protein Constituents Of The Mouse Spermatozoan", *Develop. Biol.* 75, pp. 386–404 (1980)

S. Ohno et al., "Testis-Organizing H-Y Antigen As A Discrete Protein; Its MHC Restricted Immune Recognition And The Genomic Environment In Which H-Y Gene Operates", *Hum. Genet.*, 58, pp. 37–45 (1981)

Pearson et al., "Chromosomal Studies on Human Male Gametes", *Pro. Symp. Chrom. Errors Rel. Repr. Failure*, Bove and Thibault, ed. Paris, Center Int'l. de L'Enfance pp. 219–27 (1973)

R. Peterson et al., "The Effects Of Antisperm Plasma Membrane Antibodies On Sperm-Egg Binding, Penetration, And Fertilization In the Pig", *J. Exp. Zool.*, 223, pp. 79–81 (1982) ("Peterson-I")

R. Peterson et al., "Electrophoretic And Chromatographic Properties Of Boar Sperm Plasma Membranes: Antigens And Polypeptides With Affinity For Isolated Zonae Pellucidae", *J. Androl.*, 2, pp. 300–11 (1981) ("Peterson-II")

R. Peterson et al., "The Interaction Of Living Boar Sperm And Sperm Plasma Membrane Vesicles With The Porcine Zona Pellucida", *Develop. Biol.*, 84, pp. 144–56 (1981) ("Peterson-III").

R. Peterson et al., "Evaluation Of The Purity Of Boar Sperm Plasma Membranes Prepared By Nitrogen Cavitation", *Biol. Reprod.*, 23, pp. 637–45 (1980) ("Peterson-IV)

D. Pinkel et al., "Sex Preselection In Mammals? Separation Of Sperm Bearing Y and O Chromosomes In The Vole Microtus Oregoni", *Science*, 218, pp. 904–06 (1982) ("Pinkel- I")

D. Pinkel et al. "Flow Cytometric Determination Of The Proportions of X- and Y-Chromosome Bearing Sperm In Samples Of Purportedly Separated Bull Sperm", *J. Animal Scien.*, 60, pp. 1303–07 (1985) ("Pinkel-II")

L. D. Russell et al., "Electrophoretic Map Of Boar Sperm Plasma Membrane Polypeptides And Localization And Fractionation Of Specific Polypeptide Subclasses", *Biol. Reprod.*, 28, pp. 393–413 (1983)

M. Scheid et al., "Serologically Demonstrable Alloantigens of Mouse Epidermal Cells", *J. Exp. Med.*, 135, pp. 938–55 (1972)

E. Schilling, "Sedimentation As An Approach To The Problem Of Separating X-And Y-Chromosome-Bearing Spermatozoa", *Symposium Am. Soc. Anim. Science*, pp. 76–84 (1971 )

E. Schmell et al., "Identification Of Mammalian Sperm Surface Antigens. I.Production Of Monoclonal Antimouse Sperm Antibodies", *Fertil. Steril.*, 37, pp. 249–57 (1982) ("Schmell-I")

E. Schmell et al., "Identification Of Mammalian Sperm Surface Antigens, II.Characterization Of An Acrosomal Cap Protein And A Tail Protein Using Monoclonal Antimouse Sperm Antibodies", *J. Reprod. Immunol.*, 4, pp. 91–106 (1982) ("Schmell-II")

M. Shapiro and R. P. Erickson, "Evidence That The Serological Determinant Of H-Y Antigen Is Carbohydrate", *Nature*, 290, pp. 503–05 (1981)

M. A. Shirley and H. Schachter, "Enrichment of Sulfogalactosylalkylacylglycerol in a Plasma Membrane Fraction from Adult Rat Testis", *Can. J. Biochem.*, 58, pp. 1230–39 (1980)

E Simpson, "The H-Y Antigen And Sex Reversal", *Cell* 44, pp. 813–14 (1986) ("Simpson-I")

E. Simpson et al., "Separation Of The Genetic Loci For The H-Y Antigen And For Testis Determination On Human Y Chromosome", *Nature*, 326, pp. 876–77 (1987) ("Simpson-II")

R. Stambaugh and J. Buckley, "Association Of The Lactic Dehydrogenase X4 Isozyme With Male-Producing Rabbit Spermatozoa", *J. Reprod. Fert.*, 25, pp. 275–78 (1971)

R. Stovel et al., "A Means For Orienting Flat Cells In Flow Systems", *J. Biophys.*, 23, pp. 1–5 (1978)

A. T. Sumner et al., "Distinguishing Between X, Y and YY-bearing Human Spermatozoa By Fluorescence and DNA Content" *Nature* (New Biol.), 229, pp. 231–33 (1971) S. Wachtel, "H-Y Antigen And The Genetics Of Sex Determination", *Science*, 198, pp. 797–99 (1977) ("Wachtel-I")

S. Wachtel, "Possible Role For H-Y Antigen In The Primary Determination Of Sex", *Nature* 257 pp 235–36 (1975) ("Wachtel-II")

S. Wachtel, "H-Y Antigen In The Study Of Sex Determination And Control Of Sex Ratio", *Theriog.*, 21, pp. 18–28 (1984) ("Wachtel-III")

S. Wachtel et al., "Continued Expression Of Antigen On Male Lymphoid Cells Resident In Female Mice", *Nature*, 244, pp. 102–03 (1973) ("Wachtel-IV")

S. Wachtel et al., "Serological Crossreactivity Between H-Y (male) Antigens Of Mouse and Man", *Proc. Natl. Acad. Sci. USA*, 71, pp. 1215–18 (1974) ("Wachtel-V")

P. Zavos, "Preconception Sex Determination Via Intra-Vaginal Administration Of H-Y Antisera In Rabbits", *Theriog.*, 20, pp. 235–41 (1983)

Abstracts

J. R. Schnieders and P. K. Bajpai, "Effect Of Antisperm Antibodies On Oxygen Utilization And Lactic Acid Production By Human Spermatozoa", IRCS Libr. Compend., 2, p. 1615 (1974) in *Chem. Abst.*, 82, p. 15069 (1975)

P. Soupart, "MGA-M Appearance in Ejaculated Human Sperm", *Eighth Ann. Meeting Society Study Reprod.*, Fort Collins, Co. Abstr. 133 (1975)

United States Patents

U.S. Pat. No. 3,687,806
U.S. Pat. No. 3,692,897
U.S. Pat. No. 3,906,929
U.S. Pat. No. 4,083,957
U.S. Pat. No. 4,085,205
U.S. Pat. No. 4,191,749

U.S. Pat. No. 4,448,767
U.S. Pat. No. 4,680,258
U.S. Pat. No. 4,722,887
U.S. Pat. No. 4,769,319
U.S. Pat. No. 4,770,992
U.S. Pat. No. 4,474,875

Canadian Patent 1,148,082

PCT Patent Application

WO 84/01265

European Patent Applications

EPO 251,710 A2
EPO 213,391 A

I claim:

1. A method for increasing the probability that a mammalian offspring will be female or male comprising the step of immunizing a female mammal with a Y-SAM protein or an X-SAM protein, respectively.

2. The method of claim 1 wherein the mammal is a cattle.

3. The method of claim 1 wherein the mammal is selected from the group consisting of dog, cat, horse, sheep, and pig.

4. The method of claim 1 wherein the mammal is a human.

5. A method for decreasing the fertility of a female mammal comprising the step of immunizing the female with both X-and Y-SAM proteins.

6. The method of claim 5 wherein the mammal is selected from the group consisting of dog, cat, horse, sheep, and pig.

7. The method of claim 5 wherein the mammal is a human.

* * * * *